United States Patent [19]
O'Hagan et al.

[11] Patent Number: 5,603,960
[45] Date of Patent: Feb. 18, 1997

[54] PREPARATION OF MICROPARTICLES AND METHOD OF IMMUNIZATION

[76] Inventors: Derek T. O'Hagan, 16 Middlesex Rd., Bootle, Merseyside L20 9BW, United Kingdom; John P. McGee, Tanjong Kilmarnack Rd., Kilmaurs, Strathelyde KA3 2RB, Scotland; Stanley S. Davis, 19 Cavendish Crescent North, Nottingham NG7 1BA, United Kingdom

[21] Appl. No.: 374,751
[22] PCT Filed: May 24, 1994
[86] PCT No.: PCT/US94/05834
§ 371 Date: Jun. 2, 1995
§ 102(e) Date: Jun. 2, 1995
[87] PCT Pub. No.: WO94/27718
PCT Pub. Date: Dec. 8, 1994

[30] Foreign Application Priority Data

May 25, 1993 [GB] United Kingdom ............... 9310781

[51] Int. Cl.$^6$ ............... A61K 9/50; A61K 9/48; A61K 9/14; B01J 13/02
[52] U.S. Cl. ............ 424/501; 424/451; 424/489; 264/4.1; 428/402.21; 428/402.24; 514/885; 514/963; 530/806
[58] Field of Search ............... 424/451, 489, 424/501; 264/4.1; 428/402.21, 402.24; 514/885, 963; 530/806

[56] References Cited

U.S. PATENT DOCUMENTS

| | | | |
|---|---|---|---|
| 4,389,330 | 6/1983 | Tice et al. | 427/213.36 |
| 4,532,123 | 7/1985 | Gardner | 264/4.1 |
| 4,732,763 | 3/1988 | Beck et al. | 424/433 |
| 4,897,268 | 1/1990 | Tice et al. | 424/422 |
| 5,066,436 | 11/1991 | Komen et al. | 264/4.3 |
| 5,075,109 | 12/1991 | Tice et al. | 424/1.1 |
| 5,271,945 | 12/1993 | Yoshioka et al. | 424/489 |

FOREIGN PATENT DOCUMENTS

| | | |
|---|---|---|
| 0330180 | 2/1989 | European Pat. Off. |
| 2649319 | 7/1990 | France. |
| 2234896 | 7/1990 | United Kingdom. |

OTHER PUBLICATIONS

Wise et al, *Advanced Drug Delivery Reviews* 1:19–39 (1987) "Opportunities and challenges in the design of implantable biodegradable polymeric systems for the delivery of antimicrobial agents and vaccines".

Ruiz et al, *International Journal of Pharmaceutics*, 49:69–77 (1889) "Microencapsulation of peptide: a study of the phase separation of poly(D,L,-lactic acid-co-glycolic acid) copolymers 50/50 by silicone oil".

(List continued on next page.)

*Primary Examiner*—Carlos Azpuru
*Attorney, Agent, or Firm*—Morgan & Finnegan, L.L.P.

[57] ABSTRACT

The present invention describes a method for producing microparticles useful in the formulation of pharmaceutical compositions. The present invention further describes a method of immunizing a mammal against diseases comprising administering to a mammal an effective amount of antigen containing microparticles. In particular, the present invention describes a method of potentiating an immune response in a mammal comprising administering an effective amount of a pharmaceutical composition to a mammal. The present invention further describes a vaccine comprising a pharmaceutical composition containing said microparticles. An antigen delivery system comprising microparticles containing entrapped antigens is further described by the present invention. A pharmaceutical composition comprising microparticles and a pharmaceutical carrier is also provided.

29 Claims, 4 Drawing Sheets

OTHER PUBLICATIONS

Ruiz et al, *Pharmaceutical Research* 7:928–934 (1990) "Influence of Average Molecular Weights of Poly(DL–Lactic Acid–Co–Glycolic Acid) Copolymers 50/50 on Phase Separation and In Vitro Drug Release from Microspheres".

Hora et al, *Pharmaceutical Research*, 7:1190–1194 (1990) "Release of Human Serum Albumin from Poly(lactide-co-glycolide) Microspheres".

Cohen et al, *Pharmaceutical Research* 8:713–720 (1991) "Controlled Delivery Systems for Proteins Based on Poly-(Lactic/Glycolic Acid) Microspheres".

Ruiz and Benoit, *Journal of Controlled Release*, 16:177–186 (1991) "In vivo peptide release from poly(DL–lactic acid–co–glycolic acid) copolymer 50/50 microspheres".

Wang et al, *Journal of Controlled Release* 17:23–32 (1991) "Influence of formulation methods on the in vitro controlled release of protein from poly(ester) microspheres".

Sampath et al, *International Journal of Pharmaceutics*, 78:165–174 (1992) "Preparation and characterization of biodegradable poly(L–lactic acid) gentamicin delivery systems".

PREPARATION OF MICROPARTICLES AND METHOD OF IMMUNIZATION

FIELD OF THE INVENTION

The present invention relates to a method for producing microparticles useful in the formulation of pharmaceutical compositions. The present invention further relates to a method of immunizing a mammal against diseases comprising administering to a mammal an effective amount of antigen containing microparticles. In particular, the present invention describes a method of potentiating an immune response in a mammal comprising administering an effective amount of a pharmaceutical composition containing said microparticles to a mammal. The present invention further describes a vaccine comprising a pharmaceutical composition containing said microparticles. An antigen delivery system comprising microparticles containing entrapped antigens is further described by the present invention. A pharmaceutical composition comprising microparticles and a pharmaceutical carrier is also provided.

BACKGROUND OF THE INVENTION

Interest in the administration of both therapeutic and antigenic proteins and peptides has grown considerably in recent years due to improvements in the quality and quantity of recombinant proteins and synthetic peptides now available. These molecules, however, suffer the disadvantage of having short biological half lives following parenteral administration and are degraded in the intestine following oral administration. Furthermore, if orally or nasally administered, these molecules show poor absorption through the mucous membranes.

Biodegradable polymers such as polylactide-co-glycolides (PLG) have been used to encapsulate proteins and peptides and other drugs for parenteral and/or oral delivery in order to try to achieve a stable and therapeutically adequate level of drug over an extended period of time. Previous investigators have claimed that antigenic protein and peptides can be encapsulated in microcapsules to deliver "pulses" (i.e. "intermittent doses") of antigenic material for the development of vaccines (see e.g. U.S. Pat. No. 5,075,109 to Tice et al.). The use of microencapsulation to protect sensitive bioactive agents against degradation is well known in the art, however, the use of biodegradable microparticles in controlled release delivery systems seldom results in satisfactory release profiles.

The drug release pattern for a microcapsule is dependent upon numerous factors. For example, the type of drug encapsulated and the form in which it is present (i.e. liquid or powder) may affect the drugs release pattern. Another factor which may affect the drug release pattern is the type of polymer used to encapsulate the drug. Other factors affecting the drug release pattern include the drug loading, the manner of distribution in the polymer, the particle size and the particle shape.

There are several methods known for the production of microparticles. Typical methods for producing microparticles include solvent evaporation and phase separation. With production methods such as solvent evaporation, as much as 50% w/w of insoluble or poorly soluble materials, may be incorporated in biodegradable microparticles. However, with more water soluble materials, such as peptides, drug loadings have generally been much lower.

Consequently, the use of phase separation for production of microparticles may be better suited for the formulation of microparticles containing more water soluble compounds. Phase separation methods of microparticle preparation allow a more efficient incorporation of drugs and can easily be scaled up for industrial purposes. The process of phase separation usually employs an emulsion or a suspension of the drug particles in a solution of a high molecular weight polymer and an organic polymer solvent. A non-solvent is then added to the suspension or emulsion, causing the polymer to separate from solution and to encapsulate the suspended drug particles or droplets containing them. The resulting microparticles (which are still swollen with solvent) are then normally hardened by a further addition of a non-solvent or by some other process which strengthens and improves the properties of the microparticles.

A variety of techniques to produce microparticles have been described in the prior art. For example, United Kingdom Patent Application No. 2,234,896 to Bodmer et al. describes a method of forming microparticles by mixing a solution of the polymer dissolved in an appropriate solvent with a solution of a drug. Microparticle formation is then induced by the addition of a phase inducing agent. European Patent Application 0 330 180 to Hyon et al. describes a process for preparing polylactic acid-type microparticles by adding a solution of a drug and a polymer in a mixed solvent to a phase inducing agent and evaporating the original solvent microparticle formation. Other examples of processes for preparing microparticles by phase separation technique have been described in U.S. Pat. Nos. 4,732,763 to Beck et al. and 4,897,268 to Tice et al. and by Ruiz et al. in the *International Journal of Pharmaceutics* (1989) 49:69–77 and in *Pharmaceutical Research* (1990) 9:928–934.

Despite numerous modifications to the process of polylactide-co-glycolides microparticle formation by phase separation, several problems are usually encountered when following the described techniques of microencapsulation. Such problems include: low or negligible and inefficient drug entrapment (<0.5% w.w), aggregation of particles, formation of non-spherical particles, formation of particles with surfaces that are not smooth and which have defects, the presence of large particles with a wide range of sizes (5 μm–250 μm) and the presence of non-particulate material. All these problems reduce the effectiveness and reproducability of the microparticles produced by these methods for use in controlled release delivery systems.

Traditional immunization schedules require a primary and one or more booster immunizations to achieve protective immunity. Many individuals, however, fail to receive the necessity booster immunization and therefore, fail to adequately protect themselves against the respective disease. Furthermore, this immunization regimen fails to provide a continuous dose response, leaving an individual move susceptible to diseases at one time point compared to another. Traditional immunization regimens provide an antigen to the immune system in discrete pulses. Previous investigators have attempted to convert multiple dose immunization schedules to single dose schedules using controlled release antigen delivery systems comprising biodegradable microcapsules. For example, U.S. Pat. No. 5,075,109 to Tice et al. describes a method of immunization in which the antigen is delivered in microcapsules of different sizes to attempt to provide an initial dose response followed by a subsequent dose response. The method of Tice attempts to mimic the traditional immunization regime using a single dose of the requisite antigen. Although this method alleviates the necessity for providing a booster immunization, this method does not provide a continuous administration of antigen and simply provides the traditional burst of antigen regimen.

The theory of providing continuous dose response of an antigen to elicit a prolonged immune response was discussed in 1987 by Wise et al. in *Advanced Drug Delivery Reviews* (1987) 1:19–39. Wise et al. stated that if an antigen was released in a continuous manner, the amount of antigen presented to the immune system would be too low to induce a protective immune response and may actually lead to tolerance. Recently, Walker in *Vaccine* (1994) 5:387–400 similarly stated that a sustained release of small amounts of antigen over a prolonged time period would likely induce tolerance rather than provide an effective immune response to the antigen.

The present invention solves many of the problems associated with current immunization methods. In particular, contrary to the teachings in the prior art, the present invention provides an essentially continuous release of an antigen from microparticles prepared using the novel method described by the present invention. It has been surprisingly discovered in accordance with the present invention that a continuous release of antigen results in the induction of immune responses which are comparable to those induced by the potent immunological adjuvant, aluminum hydroxide.

SUMMARY OF THE INVENTION

The present invention provides a method for producing microparticles useful in the formation of pharmaceutical compositions.

In a preferred embodiment, the average microparticle size is between 200 nm to 200 μm.

The present invention further provides a method of immunizing a mammal against diseases comprising administering to a mammal an effective amount of antigen containing microparticles.

In a preferred embodiment, the microparticles are administered orally or parenterally.

Another aspect of this invention is directed to a method of potentiating an immune response.

Yet another embodiment of the present invention provides an antigen delivery system comprising microparticles containing entrapped antigens.

Still a further aspect of the present invention provides a pharmaceutical composition comprising microparticles and a pharmaceutically acceptable carrier.

A further aspect of the present invention provides a vaccine comprising a pharmaceutical composition containing said microparticles.

DETAILED DESCRIPTION OF THE INVENTION

The present invention is directed to a method for the production of microparticles useful in the formulation of a pharmaceutical composition. In the first step to produce the microparticles described by the present invention the first medium is a non-solvent of a pharmacologically-acceptable polymer containing an aqueous solution of the bioactive material to be encapsulated (e.g. an aqueous solution of an antigen). The second medium is a solvent containing a pharmacologically-acceptable polymer dissolved in the solvent. In a second step to produce the microparticles of the present invention, the second medium is added to first medium, causing the polymer to precipitate from the solution and to microencapsulate the bioactive material as it separates, forming microparticles. Additional treatment of the microparticles such as further hardening or washing can then be carried out as appropriate.

The process of the present invention is distinguished from those in the prior art by the use of a phase-inducing agent for the formation of the dispersion of the material to be microencapsulated. This variation from the prior art leads to a process which provides microparticles of particular value. The material to be encapsulated by way of the novel process may be coated with a single wall or "shell" of polymeric material (microcapsules) or may be homogeneously dispersed within a polymeric matrix (microspheres). As defined by the present invention, the term microparticles includes both microcapsules and microspheres and the term microencapsulation or encapsulation should be construed accordingly. The novel process may be used to encapsulate a variety of materials.

In accordance with the present invention, the bioactive materials that may be encapsulated in microparticles include agricultural agents such as insecticides, fungicides, herbicides, rodenticides, pesticides, fertilizers and viruses for crop protection, as well as cosmetic agents such as deodorants and fragrances, and food additives such as flavors.

In a preferred embodiment, the microparticles of the present invention are used with pharmaceutical (bioactive) agents for prophylactic, therapeutic or even diagnostic use. The preferred pharmaceutical agents of the present invention are immunogens and drugs, especially those of a water-soluble nature. Additional preferred pharmaceutical agents include enzymes, steroids, hormones, and proteins or peptides. The most preferred pharmaceutical agents of the present invention are proteins or peptides which are antigens or portions thereof that are designed to induce an immunogenic response. In still a further preferred embodiment, the pharmaceutical agents which are recombinant proteins or synthetic peptides are microencapsulated according to the method described by the present invention.

The choice of the pharmacologically acceptable polymer and of the solvent media used to produce the microparticles of the present invention will to some extent depend upon the material to be encapsulated. When the material to be encapsulated in the microparticles is a pharmaceutical agent it is preferably encapsulated in a biodegradable polymer. As defined by the present invention a pharmacologically acceptable polymer is biocompatible as well as biodegradable (i.e.

the polymer is substantially non-toxic to the host and of such composition that it is degradable by the body into metabolic products that have no substantial deleterious or untoward effects on the body). There are many polymers described in the art which meet these criteria. For example various combinations of alpha-hydroxy-carboxylic acids and certain lactones can be condensed to form such polymers, particularly lactic acid and glycolic acids, or combinations thereof (see, for example, U.S. Pat. No. 3,773,919 to Boswell et al.). Similar biocompatible polymers based on glycolic acid and glycerol and the like are known (see, for example, U.S. Pat. Nos. 3,991,776 to Schmitt, et al. and 4,076,779 and 4,188,470 to Casey et al.). Several new biocompatible, biodegradable polymers derived from polyorthoesters and polyorthocarbonates may also be used effectively as encapsulating excipients in the practice of the present invention (see, for example, U.S. Pat. Nos. 4,093,709 and 4,138,344 to Choi et al.). There are also known polyacetals and polyorthoesters useful for this purpose. This list is not intended to be exhaustive of the polymers which are compatible with the scope and intention of this invention, but merely sets out examples to illustrate the type of polymers which may be used.

The pharmacologically acceptable polymer preferably used for encapsulating the bioactive material of the present invention is a polylactide polymer (PLA), or particularly a polylactide-co-glycolide polymer (PLG). The ratio of lactide to glycolide in the most preferred pharmacologically acceptable polymer ultimately determines the rate of release of the bioactive material from the microcapsules, and can thus be varied, depending on the desired mode of delivery of the microparticles and the contents thereof.

Generally, the molar ratio of lactide to glycolide will be between 100:0 and 0:100. In a more preferred embodiment, the molar ratio of lactide to glycolide will be preferably between 70:30 and 30:70. Thus, a preferred PLG polymer has a lactide:glycolide ratio of 50:50 and a molecular weight of 9,000 although other polymers which have been used are a PLG polymer having a lactide:glycolide ratio of 85:15 and a molecular weight of 54,000 and a PLA polymer with a molecular weight of 30,000. It is possible to administer microparticles made from more than one biodegradable polymer or made from different ratios of the same polymer. By utilizing a combination of various polymers with different lactide/glycolide ratios, the release profile of the encapsulated agent can be controlled.

The PLG polymers undergo biodegradation by random, non-enzymatic scission to form the endogenous metabolites lactic acid and glycolic acid. PLG microparticles release entrapped pharmaceutical agents as a function of time, by one or more mechanisms, but the release is mainly controlled by bulk degradation of the polymer. Depending on the composition, microparticles can be prepared that release their agent over a period of days to in excess of 1 year.

Mixed populations of PLG microparticles prepared from different polymeric compositions and molecular weights may be engineered to create an essentially continuous release of bioactive materials at predetermined intervals. For vaccination purposes, this would obviate the need for booster injections. As defined by the present invention "an essentially continuous release" describes the rate of release of the bioactive material from the microparticle into a mammal necessary to provide the required immune response to treat the requisite disease.

Microencapsulation can also be used to slow the release of a drug in the body. This has advantages in that a single essentially continuous release dose may replace several separate doses of a non-encapsulated drug. This may decrease the toxic side effects of some drugs by avoiding the high initial concentrations of drug in the blood, which often occurs following conventional administration. In some cases, it may be desirable to have an essentially continuous release pattern with the microparticles delivering a fixed amount of drug per minute, hour or day during the period of their effectiveness.

The lack of particulate material and other irregularities of shape as compared with microparticles prepared by traditional techniques means that the release profiles of microparticles prepared by the novel method of the present invention are more uniform and hence more suitable for these purposes.

When preparing microparticles by this novel method, the first medium is preferably selected from oils such as silicone oils, mineral oils, petroleum oils, sesame oil, peanut oil, soybean oil, corn oil, cotton seed oil, coconut oil and linseed oil. In a preferred embodiment, the first medium is a silicone oil. The second medium is preferably an organic solvent such as chloroform, methylene chloride, ethylene chloride, ethylene dichloride, ethyl acetate, methylchloroform, tetrahydrofuran or benzene. In a preferred embodiment, methylene chloride (dichloromethane) and in particular ethyl acetate are the second medium, especially when a PLG polymer is used.

It has been found that various other parameters of the novel process of the invention may be selected in such a way as to optimize the process. As regards the ratio by volume of the solution of polymer in the second medium, during the dispersion (as is commonly the case) of material in the first medium, it has been found that the preferred ratio lies in the range of 1:5.2 to 1:4.8. For example, a ratio of 1:5.0 is required in order to produce microparticles when using a polymer concentration of about 2% w/v. Below this range, the microparticles are less uniform; while above this range, there is an increasing tendency for matrix formation. When the polymer concentration is less than 2% w/v, the preferred ratio will move towards a smaller proportion of the polymer solution and vice versa for a polymer concentration higher than 2% w/v. In a preferred embodiment, with a polymer concentration of 3%, the preferred range of ratios is 1:3.75 to 1:3.0. With a polymer concentration of 4%, the range of ratios in the present embodiment is 1:2.72 to 1:2.3. The use of larger volumes of more concentrated polymer solution may enable a higher degree of entrapment of the material to be achieved.

As regards the temperature at which the process is carried out, it is often preferable that this is 25° C. or less, if the material to be microencapsulated is temperature sensitive, which can often be the case. However, it is preferable that the temperature is kept within a range of about 10° to 25° C., for example at 12° C. or 22° C., since below this range, the increased viscosity of the first medium can deleteriously affect microparticle formation. It is also desirable to maintain the temperature well below the boiling point of the second medium, which for dichloromethane, for example, is 40° C. The process is enhanced through the use of a surfactant, preferably one which is non-ionic such as a sorbitan ester, for example Span 40. The preferred amount of surfactant equal to about 15% by weight of the polymer.

In a preferred embodiment, the formed microparticles are further hardened in a third medium, which is desirably a non-solvent for the polymer. Such third mediums may be an alkane or halogenated alkane or a volatile silicone oil. The third medium of the preferred embodiment is heptane. The superior surface morphology which may be achieved with the microparticles of the invention may be determined by the measurement of the rugosity of the particles. The rugosity values are those measured by air permeametry. Measurement of the rugosity by air permeametry produces a value which o reflects the nature of the external surface of the material under test. The lower the rugosity value, the smoother the external surface of the microparticles. As indicated previously, the invention includes particles having a rugosity value of less than 2.0. In practice, the smoothness of the novel microparticles is readily apparent under the scanning electron microscope wherein the lack of larger particulate material may also be observed.

The average size of the microparticles produced by the novel process is between 200 nm to 200 μm characterized in that at least 90% by weight of said particles have a size which is within ±10% of the mean particle size. In a preferred embodiment, a pharmaceutical composition containing the microparticles of the present invention is administered orally or parenterally. When intended for oral administration, the microparticles are preferably between 100 nm to 10 μm in size. When intended for parenteral administration, the microparticles may be larger, preferably between 5 μm and 200 μm and especially between 10 μm and 100 μm. Parenteral administration may be by any of the normal routes, for example, intravenously, intramuscularly, intraperitoneally but is more preferably by subcutaneous injection.

The present invention further describes a composition for oral or parenteral administration comprising microparticles wherein the average size is in a range as indicated above and especially in which at least 90% by weight. In a preferred embodiment, at least 95% by weight of the microparticles have a size falling within the desired range. The composition o described by the present invention may also contain a pharmaceutically acceptable carrier. As used herein, a pharmaceutically acceptable carrier includes any and all solvents, dispersion media, coatings, antibacterial and antifungal agents, isotonic agents and the like. The use of such media and agents is well-known in the art.

The amount of pharmaceutical agent incorporated in the microparticles depends upon the starting amount of material used. Thus, it has been found that higher levels of entrapment are obtained with higher starting levels of material. Preferably, the particles contain up to 20% w/w of drug loading, conveniently between 0.01% w/w and 10% by weight of material. This amount will vary in particular with the desired dosage of a pharmaceutical agent.

It may be desirable to encapsulate bioactive agents for many purposes. Such purposes will govern the pre-use composition of the microparticle. The range of materials which may be encapsulated, particularly pharmaceutical agents, is wide and will be apparent to those skilled in the art. U.S. Pat. No. 4,389,330 to Tice et al., for example, contains a list of materials to which the novel microencapsulation process of the present invention may be applied.

The microparticles produced by the novel process of the present invention may be formulated into various forms of composition depending upon the nature of the material contained therein. Thus, when the microparticles encapsulate a pharmaceutical agent, they may be formulated into a pharmaceutical composition together with a physiologically acceptable diluent or carrier for administration. They may be administered by any means or route desired. In the case of the administration of pharmaceuticals to a patient this may be oral administration or preferably parenteral administration, especially by injection which is most preferably intramuscular or especially subcutaneous. Thus the composition may particularly be adapted for either oral or parenteral administration to a patient.

When administered parenterally, for example subcutaneously, the microparticles are preferably suspended in a pharmaceutically acceptable carrier which is sterile and pyrogen free. When administered orally, the microparticles are preferably mixed with a pharmaceutically acceptable carrier which is a solid. If the microparticles are to be administered by injection they may first be suspended in a pharmaceutically acceptable carrier. If the pharmaceutical composition is a vaccine, an adjuvant such as aluminum hydroxide may be used. The exact nature of the composition will depend upon the amount of agent to be administered, the suspending capacity of the pharmaceutically acceptable carrier and the volume of solution which can be injected at a particular site or in a particular subject.

The present invention is further directed to a method of immunizing a mammal against disease comprising administering to a mammal an effective amount of antigen containing microparticles. In particular, the present invention describes a method of potentiating an immune response in a mammal comprising administering an effective amount of a pharmaceutical composition containing said microparticles to a mammal. As defined by the present invention, an effective amount of pharmaceutical composition is the amount of composition necessary to treat the particular disease being treated. The microparticles within the composition are produced as previously described. The pharmaceutical composition may be administered orally or parenterally using conventional techniques previously described.

The present invention is also directed to an antigen delivery system comprising the microparticles described by the present invention containing an antigenic material. As used herein, the term antigenic material can include but is not limited to the desired antigen peptide, any peptides produced during the synthesis of the desired antigenic peptide, a combination of several desired peptides or the peptides produced during the synthesis of the antigenic peptides and peptides chemically linked to lipids.

The present invention also describes a vaccine comprising a pharmaceutical composition containing said microparticles. The vaccines can be administered by any of several routes including parenterally or orally in a single dose. For parenteral administration, the dose of bioactive material ranges from about 1 μg to about 500 μg. For oral administration, the dosage of bioactive material ranges from 1 μg to 10 mg. The vaccines of the present invention are administered to mammals. Moreover, the vaccine can be formulated with any other pharmaceutically acceptable carrier.

The present invention, is illustrated in the following Examples. It should be understood that the invention is not limited to the specific Examples or the details described therein. The results obtained from the experiments described in the Examples are shown in o the accompanying figures and tables.

EXAMPLE 1

Preparation of Ovalbumin-Containing Microparticles 100 mg of antigen (ovalbumin, hereinafter referred to as OVA) was suspended in 30 g of silicone oil (Dow Corning 200/1000). This was homogenized for 5 minutes with a Silverson homogenizer and then 6 ml of polylactide-co-glycolide (PLG; 50:50 lactide to glycolide ratio, m.w. 25,000 daltons) in dichloromethane (2% w/v) was added at a rate of 2 ml per minute. The mixture was homogenized throughout and for a further 1 minute after the addition of the PLG solution, cooling with methanol/liquid nitrogen to maintain the temperature at about 12° C. or 22° C. The mixture was then transferred to 300 ml of heptane and stirred for 30 minutes. The heptane was decanted and an additional 300 ml of heptane was added. The mixture was stirred for an additional 30 minutes and then decanted. The microparticles were then washed twice with 50 ml of water and recovered by centrifugation.

In a variation of the procedure described above, the 6 ml of 2% w/v PLG solution was replaced by either 9 ml of 3% w/v PLG solution or 12 ml of 4% w/v PLG solution.

In a further variation of the procedure described above, 1.15 ml of a 10% w/w dispersion of the surfactant Span 40 in water was suspended in the silicone oil together with the antigen and the whole was homogenized as described before addition of the PLG.

EXAMPLE 2

Analysis of Ovalbumin-Containing Microparticles 20 to 30 mg of dry microparticles prepared by the first method described in Example 1 were dissolved in dichloromethane and the OVA was extracted. The OVA content was then determined using a bicinchoninic acid (BCA) protein assay method. The samples were viewed under a scanning electron microscope (s.e.m.) to determine:

a. if the particles were smooth, spherical, discrete and free from surface defects;

b. whether or not there was any non-particulate material present;

c. to estimate the size and polydispersity of the particles. The size of the microparticles was confirmed by laser diffractometry using a Malvern Laser sizer 2000D. Samples were analyzed using secondary ion mass spectrometry (SIMS):

a. to determine if the OVA was present on the surface of the particles and/or if the OVA was entrapped by the polymer;

b. to show if there was any residual silicone oil in the particles.

A Western blot was carried out to determine whether or not antibodies raised to OVA still recognized OVA when run on a gel.

EXAMPLE 3

In vitro and in vivo characterization (i) In vitro release of OVA from microparticles Three batches of microparticles were prepared with polymer RG 503 containing 1.2, 2.7 and 5.1% w/w entrapped OVA and three batches were prepared with polymer R 208 containing 2.3, 3.9 and 6.5% w/w entrapped OVA. The rates of release of protein from the microparticles were determined in vitro. A known weight of microparticles (30 mg) was placed into a number of glass vials in 10 ml phosphate buffered saline and the vials were placed in a shaking water bath at 37° C. At selected intervals, one vial was removed and the buffer was filtered through a 0.2 mm filter into a clean vial and freeze dried. The levels of released OVA in the samples were assayed using a Bicinchoninic protein assay after reconstitution of the vials.

Figure 1:
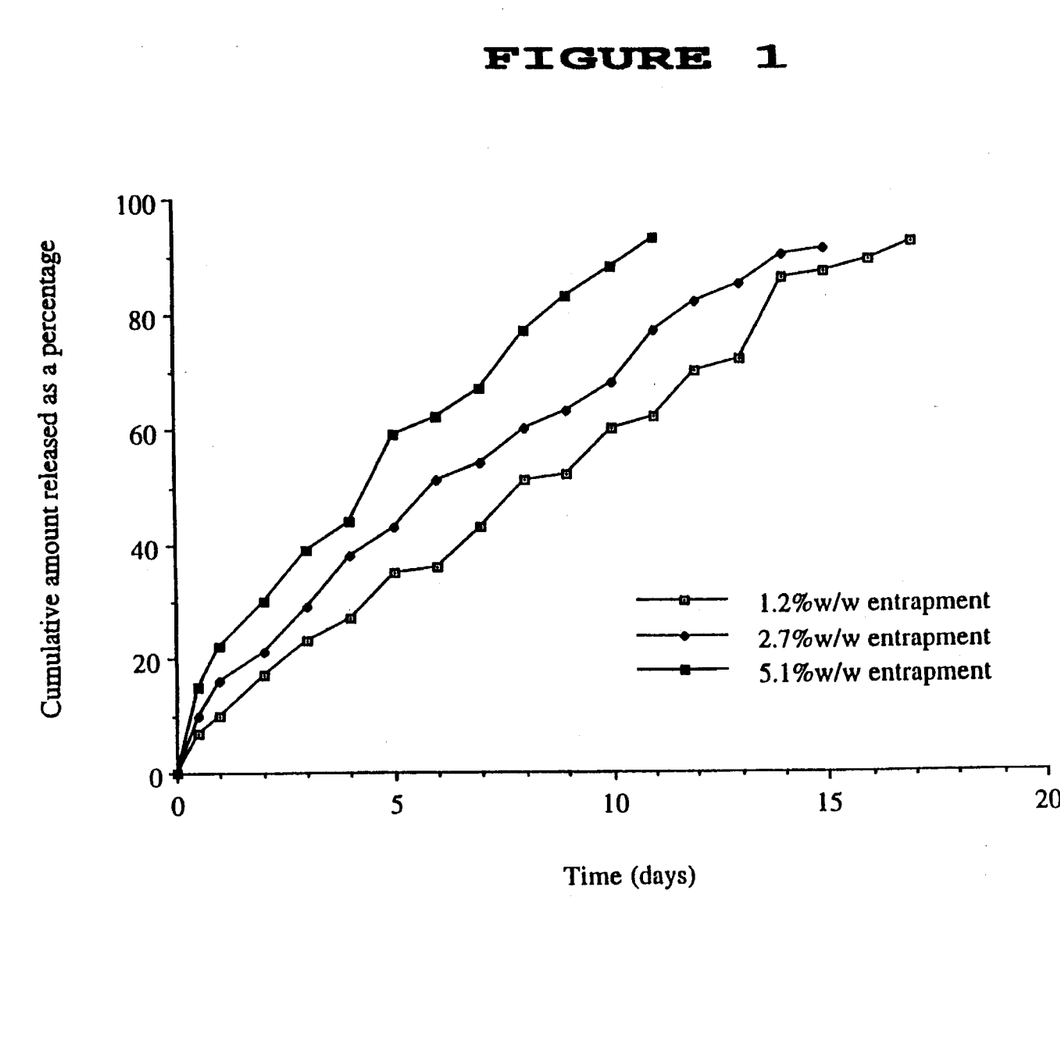
FIG. 1 shows an essentially continuous release of entrapped ovalbumin (OVA) in microparticles prepared with polymer RG 503 over 10 to 15 days in vitro.
Figure 2:
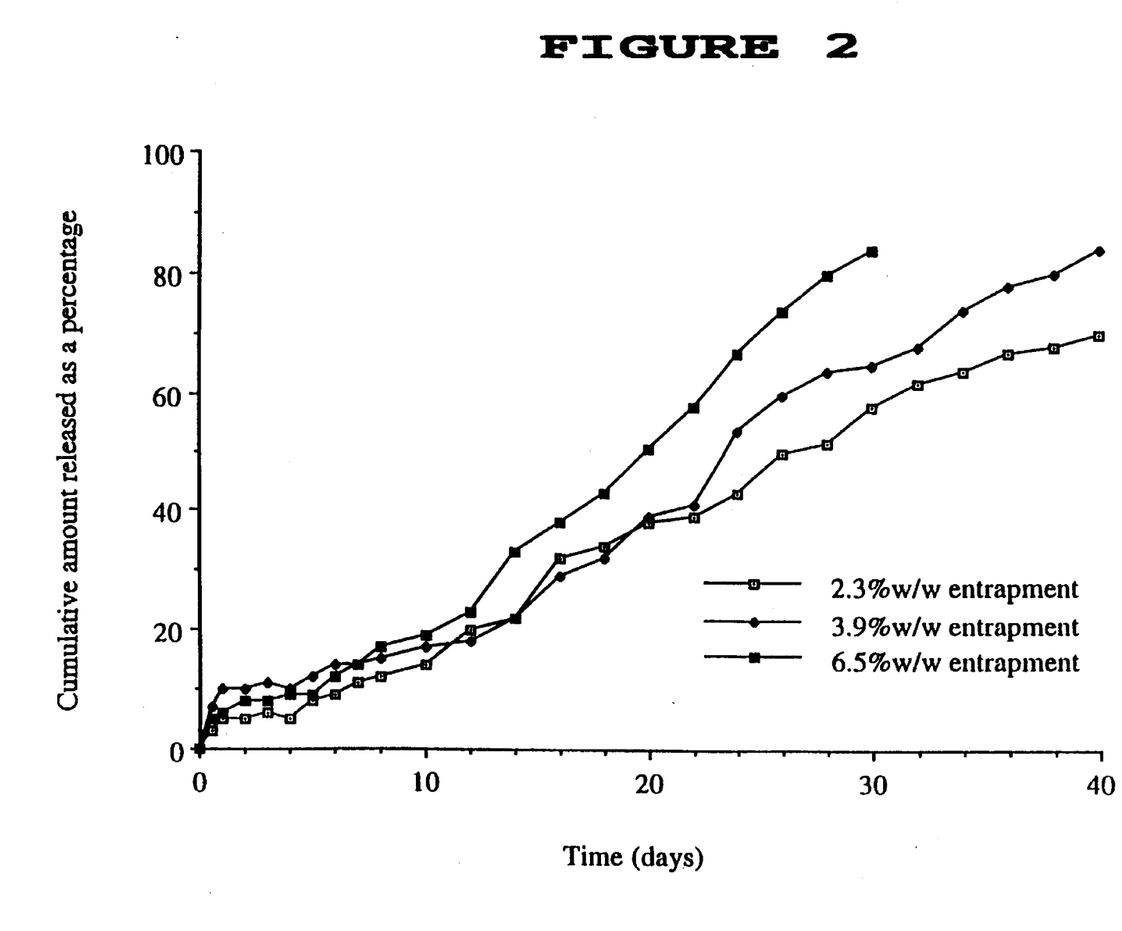
FIG. 2 shows an essentially continuous release of entrapped ovalbumin (OVA) in microparticles prepared with polymer R 208 over 40 days in vitro.

FIG. 1 shows the microparticles prepared with RG 505 using the novel phase separation technique showed a slow and steady release of entrapped OVA over 10 to 15 days in vitro. The microparticles prepared with R 208 using the novel phase separation technique showed a slow and steady release of entrapped OVA over 40 days in vitro as shown in FIG. 2. The rate of release was dependent on the level of loading and the microparticles with higher loading levels released the entrapped OVA more quickly.

(ii) In vivo studies

Parenteral immunization

Three groups of ten female BALB/c mice were each immunized subcutaneously with 100 µg OVA either entrapped in microparticles, adsorbed to a 2% suspension of alum (Alu-Gel-S, Serva, Heidelberg) or dissolved in saline. Immediately before administration the required dose of freeze dried microparticles was suspended in physiological saline. Identical booster doses were administered to each study group six weeks after the primary immunization. Blood samples were collected from the tail veins of the mice at two week intervals for twelve weeks, then every four weeks.

Oral immunization

Two groups of ten female BALB/c mice each received primary immunization with 1 mg OVA by gastric intubation on three consecutive days, either as soluble antigen, or entrapped in microparticles. Immediately before administration, the required dose of microparticles was resuspended in phosphate buffered saline. Four weeks after the primary immunizations, the two groups of animals were reimmunized with the same dose of OVA in the form previously administered. Blood samples were collected from the tail veins every two weeks.

The specific anti-OVA IgG antibody content of each serum sample was determined in an established ELISA as previously described O'Hagan in 1991 *Immunology* 73:239–242 and *Vaccine* 9:768–771 and was standardized against a positive control anti-serum obtained by hyperimmunization of a mouse with OVA in Freund's complete adjuvant. Each serum sample from each mouse was assayed at four different dilutions. The results are expressed as mean antibody units for the groups of mice, calculated from the standard curve obtained from the hyperimmune mouse serum diluted between 1/500 and 1/64,000. The value for each dilution fell on the standard curve and its value was taken as the mean of the four separate dilutions.

An unpaired students 't' test was used to compare the means at the different sample times and to assess statistical significance. Results were considered statistically significant if $p<0.05$.

Figure 3:
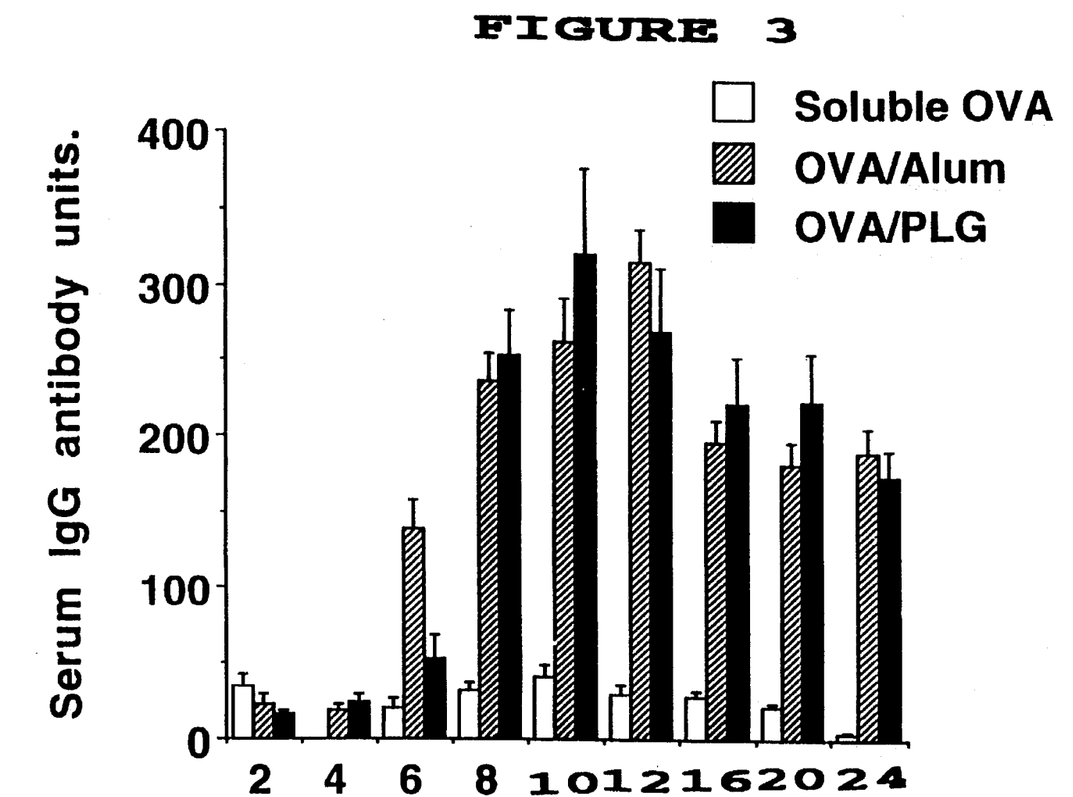
FIG. 3 shows that the serum IgG antibody response to OVA in microparticles (OVA/PLG) and the response to OVA absorbed to Alum (OVA/Alum) were significantly enhanced in comparison to the response to soluble OVA for mice parenterally immunized.

FIG. 3 shows that following booster immunizations at week six, the serum IgG antibody response to OVA in microparticles and the response to OVA adsorbed to Alum were significantly enhanced in comparison to the response to soluble OVA for mice parenterally immunized.

Figure 4:
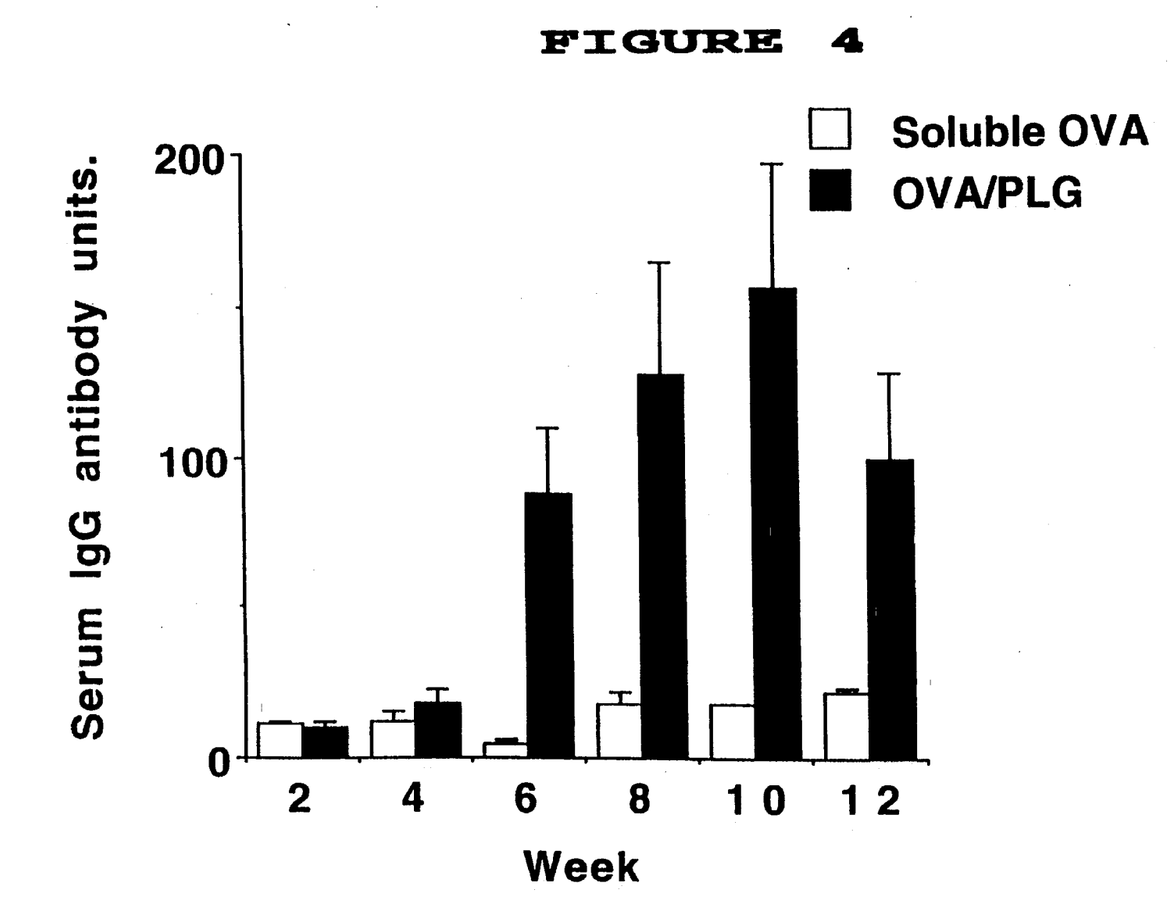
FIG. 4 shows that the serum IgG antibody response to OVA in microparticles (OVA/PLG) was significantly enhanced in comparison to the response to soluble OVA for orally immunized mice.

FIG. 4 shows that following booster immunizations at week four, the serum IgG antibody response to OVA in microparticles was significantly enhanced in comparison to the response to soluble OVA for orally immunized mice. Furthermore, following parenteral immunization, the highest antibody response (325 antibody units) was obtained at week 10 in the group administered microparticles. Thus, the present invention shows that oral immunization with microparticles induced high levels of serum antibodies that were about half the optimal levels induced by primary and secondary parenteral immunization with microparticles or alum.

The in vitro release profile of OVA from microparticles prepared by the novel preparation technique was different from the typical release profiles normally shown by proteins (Cohen et al. (1991) *Pharmaceutical Research* 8:713–720 and Hora et al. (1990) *Pharmaceutical Research* 7:1190–1194) entrapped in PLG microparticles. Studies with an alternative model protein, bovine serum albumin (BSA), entrapped in microparticles have usually shown a typical initial "burst effect" during the early stages of release. Indeed, polymer and microparticle modifications have been specifically undertaken in attempts to reduce this burst effect (Hora et al. (1990), *Pharmaceutical Research* 7: 1190–1194). The burst effect, which is thought to be due to the rapid release of surface located and poorly entrapped material, has also been shown by others for protein (Wang, (1991) *Journal of Controlled Release*, 17:23–32) and peptide (Sanders (1985) *Journal of Controlled Release*, 2:187–195 and Ruiz (1991), *Journal of Controlled Release* 16:177–186) and small molecular weight drugs (Sampath (1992) *International Journal of Pharmaceutics* 78:165–174). Although microparticle characteristics may be manipulated to minimize the burst effect, it is clear that controlled release systems prepared from PLG and related polymers normally show a release profile incorporating a substantial burst. Therefore, it is o encouraging that the novel microparticle preparation technique described in the present invention produces microparticles which display an essentially continuous release. As an illustration of this, the same protein was entrapped in microparticles prepared from the same polymer (RG 503), but prepared by a solvent evaporation technique. In an identical in vitro release study, all of the entrapped OVA was released within hours from the microparticles prepared by solvent evaporation. This contrasts sharply with the findings from the present invention, in which the entrapped OVA showed an essentially continuous release over a period of 10 to 15 days in vitro as shown in FIG. 1. Similar results were observed with a larger molecular weight polymer (R 208) and the rate of release of OVA was been controlled for 40 days in vitro as shown in FIG. 2.

In the parenteral immunization study, the microparticles showed comparable immunogenicity to an Alum-adjuvanted preparation as shown in FIG. 3. In an oral study using similar microparticles, a systemic IgG antibody response significantly greater than the response to soluble OVA was observed following a boost at four weeks as shown in FIG. 4. Prior to the boost the antibody level for the microparticle group was comparable to the soluble OVA group.

The current thinking in immunology, as discussed in the literature (e.g. Wise et al. (1987) Walker *Advanced Drug Delivery Reviews*, 1:19–39; Walker (1994) *Vaccine*, S:387–400, is that a pulsed profile of antigen release is necessary for the induction of potent immune responses and that continuous antigen release is more likely to result in the induction of tolerance or o unresponsiveness. The microparticles prepared using the novel method described in the present invention displayed a continuous release of entrapped antigen and, contrary to establish teaching in the art, induced an enhanced immune response.

Consequently, the belief that pulsed antigen release is required to induce an enhanced immune response is unfounded in light of the surprising findings obtained using microparticles prepared by the novel method as described in the present invention. These microparticles exhibited continuous release of antigen, but also induced enhanced antibody responses.

In addition it should be obvious to those skilled in the art that the release profile displayed by the model protein from the microparticles in the present study, would appear to be a potentially attractive release profile for a range of macromolecular drugs that normally require frequent injections.

While this invention has been described with reference to specific and preferred embodiments thereof, it is not limited thereto and the appended claims are intended to be construed to encompass not only the specific forms and variants of the invention shown but to such other forms and variants as may be devised by those skilled in the art without departing from the true spirit and scope of this invention.

We claim:

1. A method for producing microparticles which comprises:

dispersing a bioactive material in a first medium selected from the group consisting of silicone oils, mineral oils, petroleum oils, sesame oil, peanut oil, soybean oil, corn oil, cotton seed oil, coconut oil and linseed oil, a non-solvent for a pharmacologically acceptable polymer, adding a second medium selected from the group consisting of chloroform, methylene chloride, ethylene chloride, ethylene dichloride, ethyl acetate, methylchloroform, and tetrahydrofuran containing said polymer to said first medium, mixing the first and second media so that phase separation occurs on admixture of the two media with formation of the microparticles.

2. The method according to claim 1 wherein said microparticles when administered to a mammal release said bioactive material in an essentially continuous manner.

3. A method according to claim 1 wherein said bioactive material is an antigen.

4. The method according to claim 1 wherein said pharmacologically acceptable polymer is a biodegradable polymer.

5. The method according to claim 4 wherein said pharmacologically acceptable polymer is a polylactide-co-glycolide or a polylactide.

6. The method according to claims 1 in which the first medium is silicone oil.

7. The method according to any one of claims 1–5 in which the second medium is methylene chloride or ethyl acetate.

8. The method according to any of claims 1–5 further comprising a third medium heptane.

9. The method according to claim 1 wherein said pharmacologically acceptable polymer is composed of the dimers D,L-lactide and glycolide in which between 0 to 100% of the polymer is D,L-lactide and in which between 0 to 100% of the polymer is glycolide.

10. The method according to claim 1 wherein the average size of said microparticles administered parenterally are from 200 nm to 5 µm.

11. The method according to claim 1 wherein the average size of said microparticle administered parenterally are from 5 to 200 µm.

12. The method according to claim 1 wherein said microparticles incorporate up to 20% by weight of said material.

13. The method according to claim 1 wherein said microparticles incorporate between 0.01% and 10% by weight of said material.

14. A method for immunizing a mammal from a disease comprising administering a pharmaceutical composition containing a bioactive material entrapped in microparticles produced by:

dispersing a bioactive material in a first medium selected from the group consisting of silicone oils, mineral oils, petroleum oils, sesame oil, peanut oil, soybean oil, corn oil, cotton seed oil, coconut oil and linseed oil, a non-solvent for a pharmacologically acceptable polymer, adding a second medium selected from the group consisting of chloroform, methylene dichloride, ethylene chloride, ethylene dichloride, ethyl acetate, methylchloroform, and tetrahydrofuran containing said polymer to said first medium, mixing the first and second media so that phase separation occurs on admixture of the two media with formation of the microparticles.

15. The method according to claim 14 wherein said pharmaceutical composition is administered parenterally.

16. The method according to claim 14 wherein said pharmaceutical composition is administered orally.

17. A method for potentiating an immune response in a mammal comprising parenterally administering to said mammal microparticles produced by the process according to claim 1 and which contain an antigen.

18. The method for potentiating the immune response according to claim 17 wherein said microparticles are prepared from different polymers and batches to form a single dose of a multicomponent vaccine.

19. The method according to claim 18 wherein said microparticles are administered two or more times to said mammal.

20. The method according to claim 17 wherein said antigen is released in a continuous manner.

21. A pharmaceutical composition comprising microparticles produced by the method according to claim 1 and a pharmaceutically acceptable carrier.

22. The pharmaceutical composition according to claim 21 wherein the mean particle size of the microparticles is from 200 nm to 200 μm.

23. The pharmaceutical composition according to claim 21 wherein said composition is administered orally and said microparticles have an average size ranging from 200 nm to 5 μm.

24. The pharmaceutical composition according to claim 21 wherein said composition is administered parenterally and said microparticles have an average size ranging from 5 μm to 100 μm.

25. A vaccine comprising an antigenic pharmaceutical composition of microparticles of claim 21.

26. The vaccine according to claim 25 wherein said microparticles are comprised of a matrix which includes an antigen and a biodegradable polymer.

27. The vaccine according to claim 25 wherein said microparticles are comprised of a matrix which includes an antigen, a surfactant and a biodegradable polymer.

28. The vaccine according to claim 25 wherein the said pharmaceutical composition is administered parenterally and the dosage of bioactive material ranges from 1 μg to 500 μg.

29. The vaccine according to claim 25 wherein the said pharmaceutical composition is administered orally and the dosage of bioactive material ranges from 1 μg to 10 mg.

* * * * *